United States Patent [19]

Krimmer et al.

[11] Patent Number: 4,946,968

[45] Date of Patent: Aug. 7, 1990

[54] METHOD OF PREPARING ALKALI METAL SALTS OF 2-PYRROLIDONE-5-CARBOXYLIC ACID

[75] Inventors: Hans-Peter Krimmer, Frankfurt; Karlheinz Drauz; Hans Remmel, both of Freigericht, all of Fed. Rep. of Germany

[73] Assignee: Degussa Aktiengesellschaft, Frankfurt am Main, Fed. Rep. of Germany

[21] Appl. No.: 258,740

[22] Filed: Oct. 17, 1988

[30] Foreign Application Priority Data

Oct. 17, 1987 [DE] Fed. Rep. of Germany ....... 3735263

[51] Int. Cl.$^5$ ........................................... C07D 207/28
[52] U.S. Cl. ..................................................... 548/534
[58] Field of Search ......................................... 548/534

[56] References Cited

U.S. PATENT DOCUMENTS 3,235,563  2/1966  Noyori et al. ...................... 548/354
3,243,440  3/1966  Noyori et al. ...................... 548/354

FOREIGN PATENT DOCUMENTS 110559  9/1976  Japan ................................... 548/534

OTHER PUBLICATIONS

Lichtenstein; "Preparation of $\gamma$-Alkylamides of Glutamic Acid"; JACS 64; pp. 1021–1022 (May 1942).
Moeller, *Inorganic Chemistry;* 1976, John Wiley & Sons.
L. E. Arnow and J. C. Opsahl, "Racemization of Glutamic Acid with Heat", *Journal of Biological Chemistry,* vol. 134, pp. 649 (1940).

*Primary Examiner*—Joseph Paul Brust
*Assistant Examiner*—M. S. Howard
*Attorney, Agent, or Firm*—Cushman, Darby & Cushman

[57] ABSTRACT

Alkali metal salts of 2-pyrrolidone-5-carboxylic acid (pyroglutamic acid) are prepared by heating the corresponding alkali metal salt of glutamic acid to a temperature between its melting point and 270° C. until the water liberated by the intramolecular condensation (cyclocondensation) has been completely eliminated.

4 Claims, No Drawings

METHOD OF PREPARING ALKALI METAL SALTS OF 2-PYRROLIDONE-5-CARBOXYLIC ACID

The present invention relates to a method of preparing alkali metal salts of 2-pyrrolidone-5-carboxylic acid of the formula

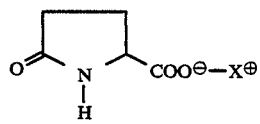
(I)

in which X+ signifies an alkali metal ion.

BACKGROUND OF THE INVENTION

The alkali metal salts of 2-pyrrolidone-5-carboxylic acid (pyroglutamic acid) are of considerable interest. For example, sodium pyroglutamate in particular is used widely as an agent for moisture retention. It is extremely hygroscopic and can absorb over 60% of its own weight of water within 30 days in air which has 65% relative humidity. A few years ago, L-sodium pyroglutamate was found to be a component of the "natural moisturizing factor" of human skin [K. Laden, R. Spitzer, "J. Soc. Cosmetic Chemists", 18, p. 351, (1967); K. Laden, "American Perfumer and Cosmetics", 82, p. 77, 1967].

Therefore, it is not surprising that sodium pyroglutamate is currently a component of numerous cosmetic products such as skin creams, hair tonics, perfumes, soaps, shampoos and toothpastes (see e.g. Japanese Patent Application JP-OS 50/25741; JP-OS 51/96808; JP-OS 55/49306 or JPOS 59/189197). Sodium pyroglutamate is also used for the moisture-retention of medical articles such as plasters and suppositories, in tobacco, in water-soluble inks or as intermediary product in chemical synthesis (see e.g. Published German Patent Application DE-OS 30 23 417).

However, in the past the synthesis of L-sodium pyroglutamate was relatively complicated. Thus, the cyclization of a mixture of L-glutamic acid and L-sodium glutamate in aqueous solution at 200° C. and elevated pressure has been described in Published Japanese Patent Application JP-OS 51/110559. A disadvantage of this method is the fact that the sodium pyroglutamate is obtained as only a 50% solution in water and that a complete racemization to D,L product, occurs. The latter is undesirable because the natural moisturizing factor consists solely of L-sodium pyroglutamate.

Another known possibility is the reaction of pyroglutamic acid with sodium hydroxide in water (see Published German Patent Application DE-OS 21 63 939); however, only an aqueous solution of the salt is produced in this instance also. Moreover, this method nevertheless requires use of L-pyroglutamic acid. Pyroglutamic acid is formed by heating L-glutamic acid in concentrated aqueous solution, but the product is racemized and the reaction results in an equilibrium of starting material and final product. A separation step is required for the synthesis of pure L-pyroglutamic acid (see P. M. Hardy, "Synthesis", 1978, p. 290). The direct heating of L-glutamic acid in the melt to 180° to 185° C. is also accompanied by racemization and, especially, by very strong decomposition (see N. Lichtenstein, S. Gertner, "J. Am. Chem. Soc." vol. 64, pages 1021-1022, 1942.

SUMMARY OF THE INVENTION

The present invention provides a method in which an alkali metal salt of glutamic acid of the formula

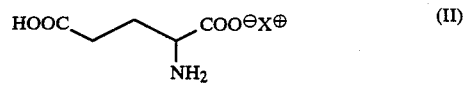
(II)

in which X+ again signifies the corresponding alkali metal ion, is heated to a temperature between its melting point and 270° C. until the water produced by the intramolecular condensation has been completely expelled.

The melting and the heating of the alkali metal salt of formula (II) can take place discontinuously or continuously, e.g. in a tubular reactor or in a spiral conveyor.

When carrying out the method of the invention, L-sodium glutamate, for example, in the form of its commercially available monohydrate, is heated in bulk, that is, in the absence of any solvent or of any other liquid heat-transferring agent, to a temperature between 220 and 270° C. A melt forms from which the water liberated by the self-condensation evaporates as gas. As soon as the initial material is completely melted, no further development of gas occurs and the L-sodium glutamate is completely converted to L-sodium pyroglutamate. The cyclocondensation occurs during the melting process. It is not at all possible to melt L-sodium glutamate and to recover it unchanged.

A slow elimination of the water of crystallization takes place even at temperatures below the melting and condensation point of L-sodium glutamate monohydrate, which is at approximately 220° C. However, this dehydration is very slow. Thus, L-sodium glutamate monohydrate can be tempered at 180° C. and 0.013 mbar for 2 days and still more than 50% of the water of crystallization can be found by the Karl Fischer method. However, a cyclization to L-sodium pyroglutamate does not yet take place.

The duration of the melting process depends on the external temperature and the heat transfer capacity of the reaction vessel. Whereas 30 grams of L-sodium glutamate monohydrate require approximately 60 minutes at an oil bath temperature of 220° C. to melt completely, this process takes only one minute for the same quantity in a metal vessel at an oil bath temperature of 270° C. After having cooled off, the L-sodium pyroglutamate melt hardens to a colorless, brittle glass. If the temperature is not maintained longer than one hour over 250° C. or if the temperature is not briefly raised over 270° C., no racemization or formation of by-products occurs.

For analytic or preparative purposes, a diluted, aqueous solution of L-sodium pyroglutamate can be desalinated over a strongly acidic ion-exchange column (e.g. Duolite C26) and the free L-pyroglutamic acid is quantitatively obtained after removal of the water under reduced pressure.

The lithium, potassium, rubidium and cesium salts of glutamic acid can also be used as starting materials for the method of the invention. Each of these salts exhibits a characteristic melting range in which the cyclocondensation occurs. This melting range is usually between 210 and 270° C.

The invention is illustrated in more detail in the following examples:

EXAMPLE 1

30.0 g (0.160 mole) L-sodium glutamate monohydrate were immersed in a 250 ml round flask into an oil bath preheated to 220° C. After 5 minutes, the crystallizate started to adhere and water vapor developed. A colorless melt slowly formed which vigorously emitted gas. After one hour, the crystallizate wa completely converted into a thin melt and the liberation of gas ceased. The melt was poured into a cold porcelain dish and hardened to a brittle, colorless glass. After grinding, a colorless, very hygroscopic powder resulted which melted at 125° C. An HPLC analysis (NH$_2$ column, 3 μm, 250×4.6 mm; mobile solvent: acetonitrile/0.05 M KH$_2$PO$_4$(6:4; v/v), UV detector 210 nm) of the product showed complete conversion into L-sodium pyroglutamate (Rt=7.14). L-sodium glutamate (RT=13.42) could no longer be detected even in trace amounts. The yield was 24.0 g (99% of theory).

For conversion into L-pyroglutamic acid, 10 g of the product were dissolved in 200 ml water passed through an ion-exchange column (Duolite C26, H$^+$ form; 11 cm × 2.5 cm; 30 g). After elution and removal of the water under reduced pressure, 8.5 g (quantitative) L-pyroglutamic acid were produced with a melting point of 155–157° C. [Cf. H Gibian, E. Klieger, "Liebigs Ann. Chem.", 640, p. 145, (1961): melting point: 156–157° C.].

$[\alpha]^{25}_D$: −11.6.° (c=4, H$_2$O) [Cf. A. C. Kibrick, "J. Biol. Chem.", 174, p. 845, (1948): $[\alpha]^{25}_D$−11.7° (c=4, H$_2$O)].

EXAMPLE 2

30 g L-sodium glutamate monohydrate were added, all at once, to a steel cylinder closed at the bottom (20 cm × 5 cm) which was immersed in an oil bath preheated to 270° C. and which had assumed the temperature of the oil bath. The initial product melted within one minute with vigorous development of water vapor. The further work-up and characterization took place in a manner which was analogous to Example 1.

EXAMPLE 3

30 g (0.196 mole) L-lithium glutamate were melted at 270° C. in a manner analogous to Example 1. 25.4 g (96% of theory) L-lithium pyroglutamate were produced.

EXAMPLE 4

30 g (0.162 mole) L-potassium glutamate were melted at 210° C. in a manner which was analogous to Example 1. 27 g (99% of theory) of very hygroscopic L-potassium pyroglutamate were produced.

EXAMPLE 5

2.0 g (8.64 mmoles) L-rubidium glutamate were melted at 210° C. in a manner which was analogous to Example 1. 1.8 g (98% of theory) L-rubidium pyroglutamate were produced.

EXAMPLE 6

2.0 g (7.17 mmoles) L-cesium glutamate were melted at 210° C. in a manner which was analogous to Example 1. 1.8 g (96% of theory) L-cesium pyroglutamate were obtained.

What is claimed is:

1. A method of preparing alkali metal salts of L-2-pyrrolidone-5-carboxylic acid of the formula

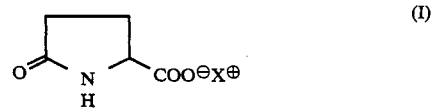 (I)

in which X$^+$ signifies an alkali metal ion, said method consisting of heating an alkali metal salt of L-glutamic acid of the formula

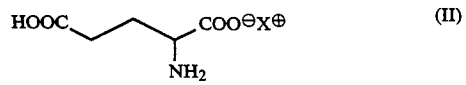 (II)

in which X$^+$ signifies the corresponding alkali metal ion in bulk to a temperature between about 210° C. and 270° C. until the water produced by the intramolecular condensation has been completely eliminated.

2. A method as set forth in claim 1 in which the melting and the heating take place discontinuously.

3. A method as set forth in claim 1 in which the melting and the heating take place continuously.

4. A method as set forth in claim 1 in which the alkali metal is sodium and the temperature of the reaction is between 220 and 270° C.

* * * * *